(12) United States Patent
Osypka

(10) Patent No.: US 6,738,674 B2
(45) Date of Patent: May 18, 2004

(54) IMPLANTABLE CORONARY SINUS LEAD WITH MAPPING CAPABILITIES

(75) Inventor: Thomas P. Osypka, Palm Harbor, FL (US)

(73) Assignee: Oscor Inc., Palm Harbor, FL (US)

( * ) Notice: Subject to any disclaimer, the term of this patent is extended or adjusted under 35 U.S.C. 154(b) by 318 days.

(21) Appl. No.: 10/058,489

(22) Filed: Jan. 28, 2002

(65) Prior Publication Data

US 2003/0023296 A1 Jan. 30, 2003

Related U.S. Application Data

(63) Continuation-in-part of application No. 09/912,796, filed on Jul. 25, 2001, which is a continuation-in-part of application No. 10/000,647, filed on Nov. 1, 2001.

(51) Int. Cl.$^7$ .................................................. A61N 1/05
(52) U.S. Cl. ........................ 607/122; 600/374; 600/439; 600/455; 600/468
(58) Field of Search ................................. 607/119, 122, 607/123; 600/377, 374, 439, 453, 454, 459, 462, 465, 467, 468, 526, 505, 455

(56) References Cited

U.S. PATENT DOCUMENTS

| 4,458,677 A | 7/1984 | McCorkle, Jr. |
| 5,129,394 A | 7/1992 | Mehra |
| 5,190,045 A * | 3/1993 | Frazin ........................ 600/463 |
| 5,409,009 A | 4/1995 | Olson |
| 5,534,022 A | 7/1996 | Hoffmann et al. |
| 5,554,176 A | 9/1996 | Maddison et al. |
| 5,628,779 A | 5/1997 | Bornzin et al. |
| 5,738,683 A | 4/1998 | Osypka |
| 5,860,920 A | 1/1999 | McGee et al. |
| 5,925,073 A | 7/1999 | Chastain et al. |
| 5,951,597 A | 9/1999 | Westlund et al. |
| 5,964,795 A | 10/1999 | McVenes et al. |
| 6,216,043 B1 | 4/2001 | Swanson et al. |
| 6,233,491 B1 | 5/2001 | Kordis et al. |
| 6,254,599 B1 | 7/2001 | Lesh et al. |
| 6,277,108 B1 | 8/2001 | McBroom et al. |

OTHER PUBLICATIONS

International Search Report dated Apr. 17, 2003.

* cited by examiner

Primary Examiner—Kennedy Schaetzle
(74) Attorney, Agent, or Firm—Scott D. Wofsy; Edwards & Angell, LLP

(57) ABSTRACT

A cardiac lead is disclosed that includes a first lead body having opposed proximal and distal end portions and an interior lumen extending therethrough. The first lead body includes a sensor for measuring blood flow parameters to facilitate placement of the distal end portion thereof adjacent the coronary sinus. The first lead body has a distal electrode operatively associated with the distal end portion thereof and a proximal electrode operatively associated with the proximal end thereof. The second lead body has opposed proximal and distal end portions. A distal electrode is operatively associated with the distal end portion thereof and a proximal electrode operatively associated with the proximal end thereof. The second elongated lead body is dimensioned and configured for accommodation within the interior lumen of the first lead body.

17 Claims, 9 Drawing Sheets

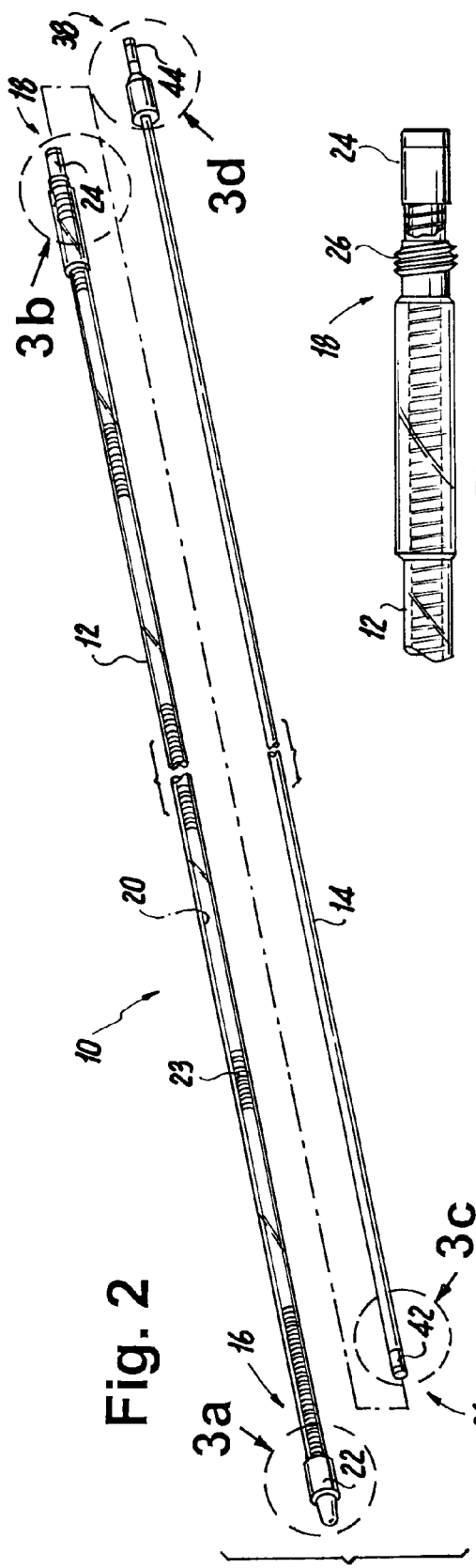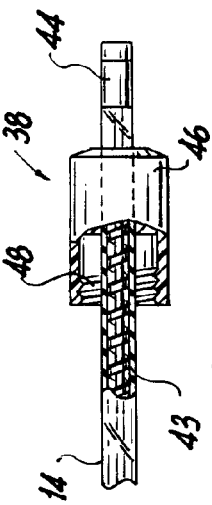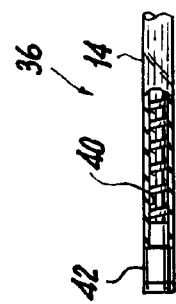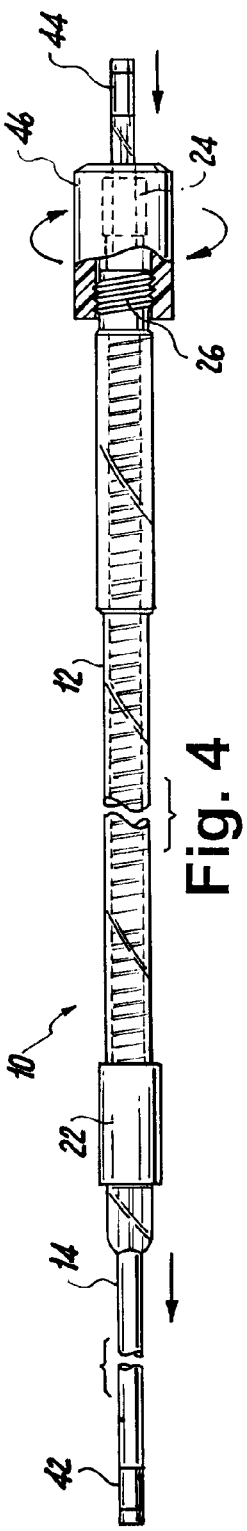

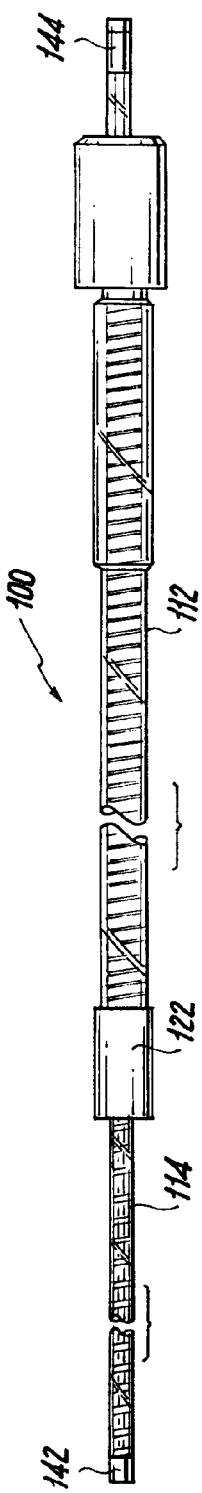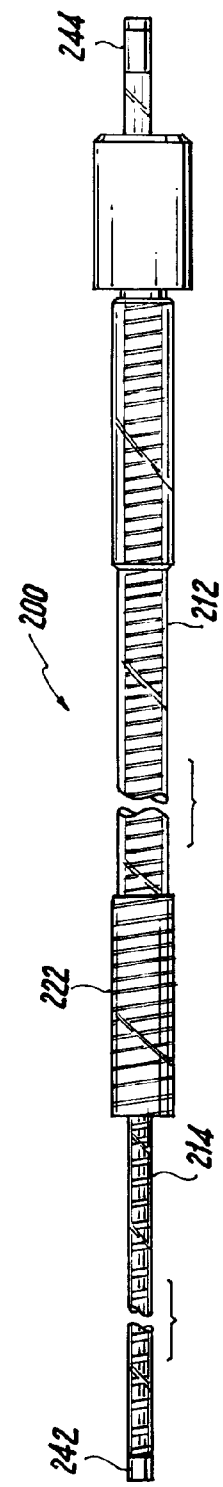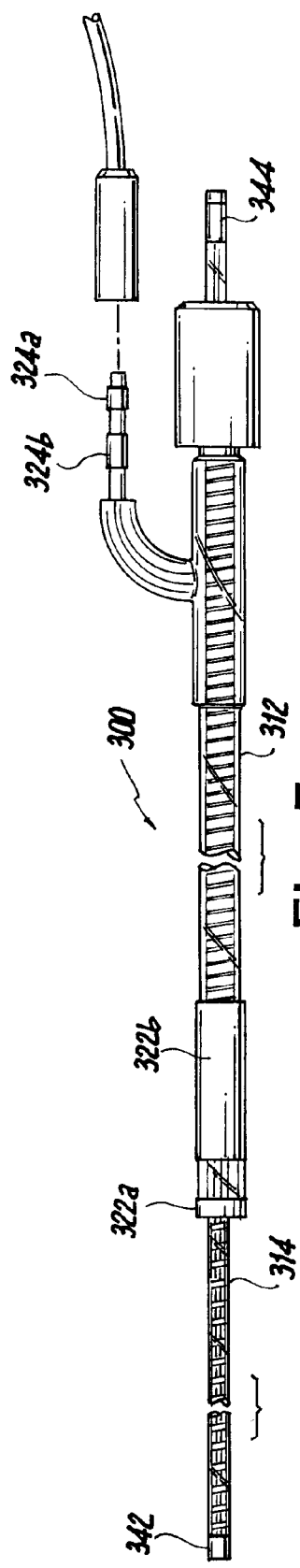

IMPLANTABLE CORONARY SINUS LEAD WITH MAPPING CAPABILITIES

CROSS-REFERENCE TO RELATED APPLICATIONS

The subject application is a continuation-in-part of U.S. application Ser. No. 09/912,796 filed Jul. 25, 2001 and a continuation-in-part of U.S. application Ser. No. 10/000,647 filed Nov. 11, 2001.

BACKGROUND OF THE INVENTION

1. Field of the Invention

The subject invention is directed to an intravenous lead, and more particularly, to an implantable cardiac lead and having mapping capabilities to facilitate safe placement of the lead within the coronary sinus.

2. Background of the Related Art

Electrical therapeutic and diagnostic devices for the heart, such as pacemakers and defibrillators, commonly employ leads for connecting an electrical pulse generator to excitable cardiac tissue, usually within the right ventricle and/or right atrium. Pacing and defibrillation leads commonly include one or more distal electrodes and often have outwardly projecting tines near the distal tip or an active fixation screw to hold the electrode in contact with endocardial tissue in the right ventricle or atrium.

It has been found that cardiac stimulation can have a beneficial effect in treating congestive heart failure. However, pacing therapy for treating congestive heart failure often requires left ventricular stimulation, either alone or in conjunction with right ventricular stimulation and defibrillation. Left ventricular pacing presently requires placement of an epicardial lead by way of a thoracotomy, which is a high risk procedure performed under general anesthesia. To obviate the need for a thoracotomy, left ventricular access leads have been developed which are introduced through the coronary sinus and then advanced through the coronary veins so that the distal electrode of lead can be positioned on the surface of the left ventricle near the apex of the heart.

The coronary veins of the heart are of a relatively small diameter. The lead extended therethrough must therefore, be of a relatively small diameter, as compared to leads used for right ventricular stimulation. Cardiac and respiratory motion as well as blood flow can cause a lead to become dislodged. Accordingly, the lead must include structure to anchor the electrode at a desired location.

It would be beneficial to provide a left ventricular pacing lead configured for advancement through the coronary sinus and into the coronary vein, which has structure for anchoring the distal end of the lead at a desired site of stimulation, and which could be used in certain instances for defibrillation.

SUMMARY OF THE INVENTION

The subject invention is directed to a new and useful implantable cardiac lead adapted and configured for advancement through the coronary sinus and into the coronary vein that includes cooperating first (outer) and second (inner) elongated lead bodies. The first lead body has opposed proximal and distal end portions, an interior lumen extending therethrough, at least one distal electrode operatively associated with the distal end portion thereof and a proximal electrode operatively associated with the proximal end thereof. Preferably, the first lead body includes sensor means that are operatively associated with the distal end portion thereof for measuring blood flow parameters to facilitate placement of the distal end portion of the first lead body adjacent the coronary sinus, and seal means for sealing the interior lumen of the first lead body during insertion of the first lead body through the coronary venous system.

The second (inner) lead body has opposed proximal and distal end portions, at least one distal electrode operatively associated with the distal end portion thereof, a proximal electrode operatively associated with the proximal end thereof, and it is dimensioned and configured for accommodation within the interior lumen of the first (outer) lead body. Preferably, the proximal end portion of the first lead body and the proximal end portion of the second lead body include means for connecting the first lead body to the second lead body.

In accordance with the subject invention, the second lead body has a length that is greater than the length of the first lead body. Preferably, the length of the first lead body is about between 50 and 80 cm, and the length of the second lead body is about between 60 and 100 cm. preferably, the outer diameter of the first lead body is about between 6 and 9 F, and the outer diameter of the second lead body is about between 3 and 5 F.

A conductor extends through the first lead body to connect the distal electrode and the proximal electrode, and a conductor extends through the second lead body to connect the distal electrode and the proximal electrode. Additionally, the second lead body has an interior lumen extending therethrough to accommodate a stylet. In one embodiment of the invention, the distal electrode of the first lead body is a ring electrode spaced from the distal end of the lead body for pacing and/or sensing. Alternatively, the distal electrode of the first lead body is a coil electrode used for defibrillation, or as a ground electrode. In one embodiment of the invention, the distal electrode of the second lead body is a ring electrode that is spaced from the distal end of the second lead body for pacing and/or sensing. Alternatively, the distal electrode of the second lead body is configured as tip electrode for pacing and/or sensing. The proximal electrode of the second lead body is preferably defined as a pin connector.

The second or inner lead body preferably has fixation means operatively associated with the distal end portion thereof for anchoring the lead within the coronary venous system. In addition, the first or outer lead body may have fixation means operatively associated with the distal end portion thereof. In either case, the fixation means may be defined by at least one radially expandable tine, by an expandable stent configured for movement between a retracted position and an expanded position, or by a plurality of radially expandable arms configured for movement between a retracted position and an extended position. Furthermore, the fixation means may have a coating containing a medicament such as a steroid.

The subject invention is also directed to a new and useful method of implanting a cardiac lead comprising the steps of passing an elongated outer lead body having an interior lumen through the venous system to a selected coronary vein, and extending an elongated inner lead body into the interior lumen of the outer lead body so that a distal end portion of the inner lead body extends from a distal end portion of the outer lead body.

The method further includes that steps of securing the inner and outer lead bodies to one another, and anchoring at least one of the distal end portion of the inner lead body and the distal end portion of the outer lead body within the selected coronary vein. The step of anchoring at least one of the distal end portion of the inner lead body and the distal end portion of the outer lead body within the selected coronary vein includes deploying an expandable stent operatively associated with at least one of the distal end portion of the inner lead body and the distal end portion of the outer lead body, or deploying expandable arms operatively associated with at least one of the distal end portion of the inner lead body and the distal end portion of the outer lead body.

These and other aspects of the subject invention and the method of using the same will become more readily apparent to those having ordinary skill in the art from the following detailed description of the invention taken in conjunction with the drawings described hereinbelow.

BRIEF DESCRIPTION OF THE DRAWINGS

So that those having ordinary skill in the art to which the subject invention pertains will more readily understand how to make and use the cardiac lead of the subject invention, preferred embodiments thereof will be described in detail hereinbelow with reference to the drawings, wherein:

FIG. 2 is a perspective view of the two-part coronary sinus lead of the subject invention which includes an outer lead body having an anodic ring electrode associated with the distal end portion thereof, and an inner lead body configured for accommodation within the interior lumen of the outer lead body and having a cathodic tip electrode associated with the distal end thereof;

FIG. 3a is a side-elevational view, in partial cross-section, of the distal end portion of the outer lead body, with the tapered distal tip thereof in an initially sealed condition to facilitate ease of intra-vascular introduction;

FIG. 3b is a side elevational view, in partial cross-section, of the proximal end portion of the outer lead body;

FIG. 3c is a side elevational view, in partial cross-section, of the distal end portion of the inner lead body;

FIG. 3d is a side elevational view, in partial cross-section, of the proximal end portion of the inner lead body;

FIG. 4 is a side elevational view of the coronary sinus lead of the subject invention, with the proximal coupling of the inner lead body partially sectioned to illustrate the threaded engagement of the proximal end portions of the inner and outer lead bodies;

FIG. 5 is a side elevational view of another embodiment of the coronary sinus lead of the subject invention configured for left ventricular pacing and sensing;

FIG. 6 is a side elevational view of another embodiment of the coronary sinus lead of the subject invention configured for left ventricular pacing and sensing, and for right ventricular defibrillation;

FIG. 7 is a side elevational view of another embodiment of the coronary sinus lead of the subject invention configured for left ventricular pacing and sensing, and for right atrial pacing and sensing.

DETAILED DESCRIPTION OF PREFERRED EMBODIMENTS

Figure 1:
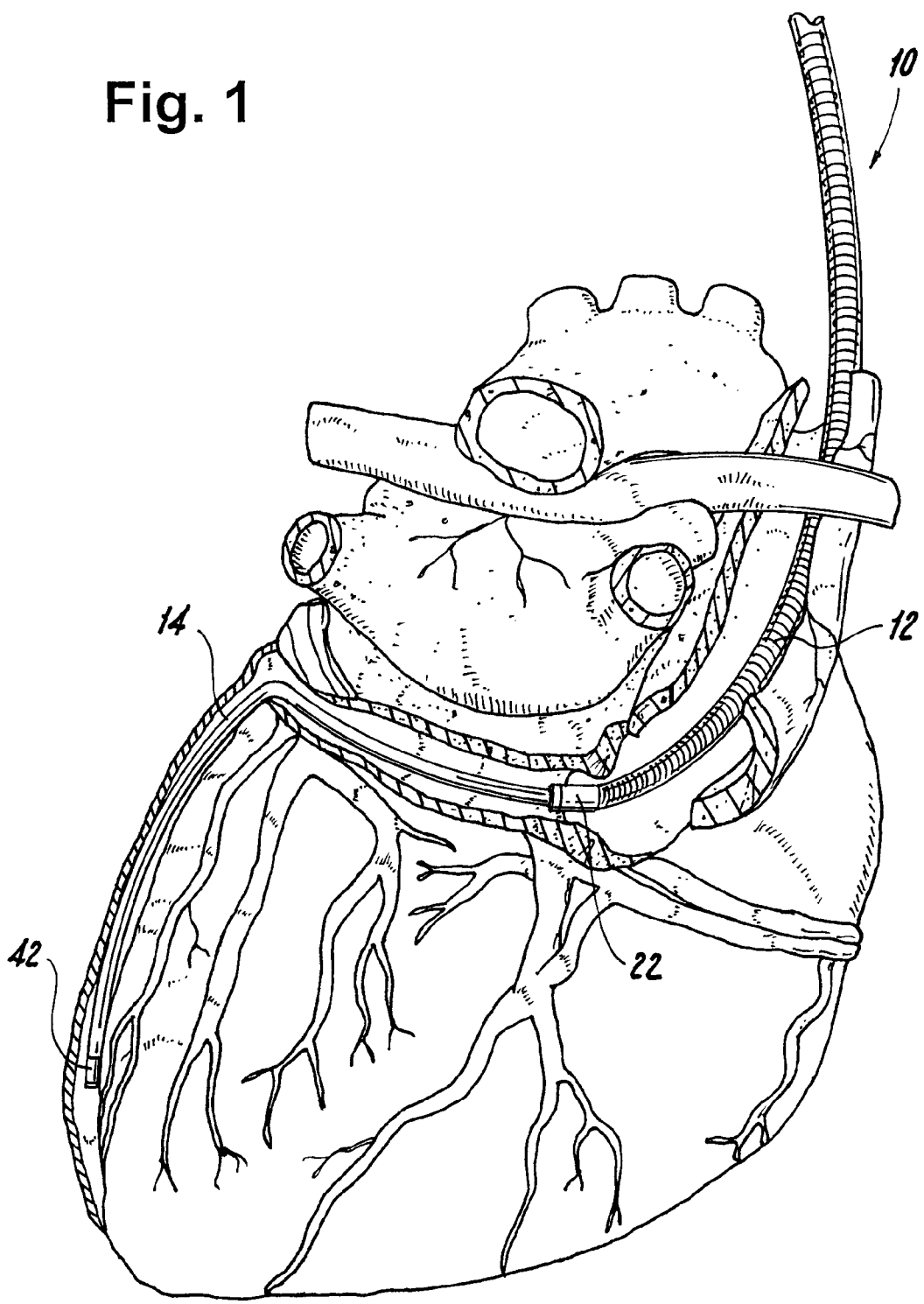
FIG. 1 is a perspective view of the two-part coronary sinus lead constructed in accordance with a preferred embodiment of the subject invention, the distal end of which is in electrical contact with the left ventricle of the heart through the great cardiac vein.

Referring now to the drawings wherein like reference numerals identify similar structural features of the intravenous leads disclosed herein, there is illustrated in FIG. 1 a coronary sinus lead constructed in accordance with a preferred embodiment of the subject invention and designated generally by reference numeral 10. Coronary sinus lead 10 is adapted and configured for intravenous introduction to the great cardiac vein or branch vein through the coronary sinus so that an electrode associated with a distal end portion of the lead is in electrical contact with the left ventricle of the heart. The proximal end of the lead is then operatively connected to an implanted therapeutic electrical device such as a pacemaker. Once in contact, the distal electrode of lead 10 may be employed for left ventricular pacing and/or sensing.

Referring to FIGS. 2 and 3a–3b, coronary sinus lead 10 includes an outer lead body 12 and an inner lead body 14 configured for reception and accommodation within an interior lumen of the outer lead body. More particularly, the outer lead body 12 has opposed distal and proximal end portions 16 and 18, and an interior lumen 20 extending therethrough. The distal end portion 16 of lead body 12 is tapered to ease the intravascular placement thereof. A distal electrode 22 is operatively associated with the distal end portion 16 and a proximal electrode 24 is operatively associated with the proximal end portion 18. The distal electrode 22 is in the form of a ring electrode, as is the proximal electrode 24. However, other types of electrode configurations can be employed for purposes other than sensing and/or pacing as will be described in more detail hereinbelow. The proximal and distal electrodes 22, 24 of the outer lead body 12 are electrically connected to one another by a conductor such as a monofilliar or multifilliar coil 23, and they serve as the anode for coronary sinus lead 10. The proximal end portion 18 of the outer lead body 12 has a connective device operatively associated therewith for cooperating with a complimentary structure on the proximal end portion of the inner lead body 14. More particularly, the proximal end portion 18 of the outer lead body 12 has a helical thread 26 formed on an exterior surface thereof, spaced from or formed integral with the proximal electrode 24.

Referring to FIGS. 2 and 3c–3d, the inner lead body 14 has opposed distal and proximal end portions 36 and 38 and an interior lumen 40 for accommodating a stylet (not shown) to guide placement of the lead in the great cardiac vein. The inner lead body 14 has a distal electrode 42 operatively associated with the distal end portion 36 and a proximal electrode 44 operatively associated with the proximal end portion 38. The distal electrode 42 is in the form of a ring electrode, as is the proximal electrode 44. However, other types of electrode configurations can be employed for purposes other than sensing and/or pacing as will be described in more detail hereinbelow. Proximal electrode 44, for example, can be configured as a connector pin with an axial bore for accommodating passage of a stylet. The proximal and distal electrodes 42, 44 of the inner lead body are electrically connected to one another by a conductor such as a monofiliar or multifiliar coil 43, and they serve as the cathode for coronary sinus lead 10. The proximal end portion 38 of the outer lead body 14 has a connective device in the form of an end cap 46 with an interior helical thread 48 for cooperating with the helical thread 26 associated with the proximal end portion 18 of outer lead body 12.

It is envisioned that the conductor coils 23, 43 used to connect the respective distal and proximal electrodes of the inner and outer lead bodies could be formed from an insulated wire. The wire could be a low resistance wire such as, for example, MP35N or DFT wire, and the insulative coating could be PTFE, polyamide, silicone or a similar material.

Those skilled in the art will readily appreciate that alternative mechanisms may be employed to interconnect the proximal ends of the outer and inner lead bodies 12, 14 without departing from the spirit or scope of the subject disclosure. Moreover, the illustrated threaded connective mechanism, which is referred to in the art as an IS-1 type connector, is merely an example of a connector that may be employed with the inner and outer lead bodies 12, 14.

As illustrated in FIG. 4, the inner lead body is dimensioned and configured for accommodation within the interior lumen 20 of the outer lead body in such a manner so that the distal end portion 36 of the inner lead body 14 extends from the distal end portion 16 of the outer lead body 12. In particular, the length of the outer lead body 12 is about between 50 and 80 cm, and the length of the inner lead body 14 is about between 60 and 100 cm. Thus, the distal end portion 36 of the inner lead body 14 extends from the interior lumen 20 of the outer lead body about between 10 and 20 cm. The outer diameter of the outer lead body 12 is about between 6 and 9 F, and the outer diameter of the inner lead body 14 is about between 3 and 5 F. Those skilled in the art will readily appreciate that the dimensions disclosed herein could vary without departing from the scope of the invention.

Referring now to FIG. 5, there is illustrated another coronary sinus lead constructed in accordance with a preferred embodiment of the subject invention and designated generally by reference numeral 100. Coronary sinus lead 100 is similar to coronary sinus lead 10 in that it is configured for left ventricular pacing and sensing. Lead 100 differs however in that the outer lead body 112 includes a distal ground electrode 122 and the inner lead body 114 includes a distal tip electrode 142.

FIG. 6 illustrates another coronary sinus lead constructed in accordance with a preferred embodiment of the subject invention and designated generally by reference numeral 200. Coronary sinus lead 200 is configured for left ventricular pacing and sensing, and for right ventricular defibrillation. More particularly, the inner lead body 214 includes a distal tip electrode 242 (in conjunction with proximal ring electrode 244) for pacing and/or sensing, and the outer lead body 212 includes an elongated distal ground electrode or coil 222 for facilitating right ventricular defibrillation in conjunction with a second cardiac lead which will be discussed in greater detain hereinbelow with reference to FIG. 14.

FIG. 7 illustrates yet another coronary sinus lead constructed in accordance with a preferred embodiment of the subject invention and designated generally by reference numeral 300. Coronary sinus lead 300 is configured for left ventricular pacing and sensing, and for right atrial pacing and sensing. More particularly, the inner lead body 314 has a distal tip electrode 342 for pacing and/or sensing, and the outer lead body 312 includes distal ring electrode 322a for right atrial pacing/sensing and an elongated distal ground electrode 322b for facilitating right ventricular defibrillation in conjunction with a second cardiac lead which will be discussed in greater detain hereinbelow with reference to FIG. 15. In this embodiment, proximal ring electrode 344 is provided on inner lead body 314 and proximal ground an right atrial electrodes 324a and 324b are associated with outer lead body 312.

The tip, ring and ground electrodes employed on the inner and outer lead bodies are preferably formed from a platinum/iridium alloy, as is the coiled shock electrode. The inner and outer lead bodies are preferably formed from silicon, polyurethane, PTFE or a similar bio-compatible insulative plastic or elastomer.

In accordance with an embodiment of the subject invention, the coronary sinus lead includes a fixation member operatively associated with the distal end portion of the inner lead body. The fixation member is adapted and configured to anchor the lead within the coronary sinus against the flow of blood and the cardiac pressure of the beating heart. Preferably, the fixation member has a polymeric coating containing a medicament that is released into the vascular tissue over time. The polymeric coating is preferably absorbable, and the medicament is preferably a steroid or a similar therapeutic drug for treating the cardiac tissue surrounding the distal end of the lead. Non-polymeric coating s may also be used to carry a medicament for absorption. It is also envisioned that the fixation member can be electrically active so as to function as a distal electrode for pacing and/or sensing.

Figure 10A:
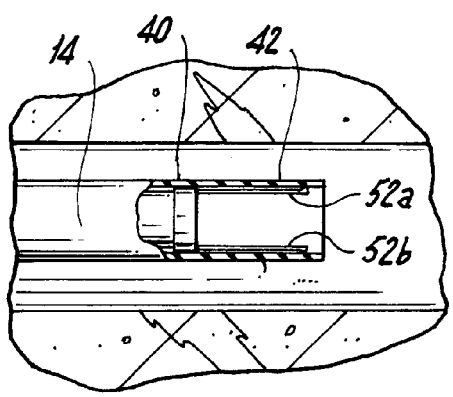
FIGS. 10a and 10b illustrate the retracted and extended positions, respectively, of an anchoring device associated with the distal end portion of the inner lead body.
Figure 10B:
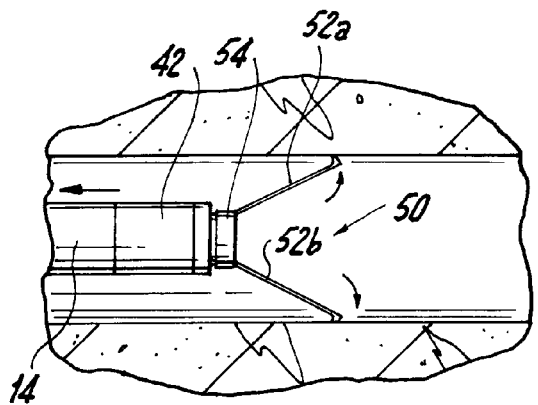

Referring to FIGS. 10a–10b, one embodiment of the fixation member is designated generally by reference numeral 50. Fixation member 50 includes a pair of radially expandable arms 52a and 52b which extend from an annular base structure 54. The arms 52a, 52b are formed from a bio-compatible material, such as stainless steel, or a shape memory metal such as a nickel-titanium alloy. Fixation member 50 is operatively associated with the distal end portion 36 of the inner lead body and is mounted for movement between a retracted position (FIG. 10a) wherein arms 52a, 52b are disposed within the interior lumen 40 of inner lead body 14 and an extended position (FIG. 10b) wherein arms 52a, 52b extend radially outwardly to anchor lead body 14 against longitudinal displacement. In use, fixation member 50 may be deployed from the retracted position to the extended position by extending an elongated stylet or similar structure through the interior lumen 40 of inner lead body 14. It is envisioned that the distal end of lumen 40 would be adapted to limit the movement of the base structure 54 beyond a certain point to maintain it within the interior lumen.

Figure 11A:
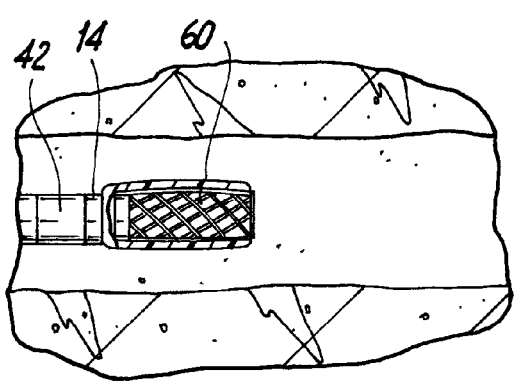
FIGS. 11a and 11b illustrate the contracted and expanded positions, respectively, of an expandable stent operatively associated with the distal end portion of the inner lead body.
Figure 11B:
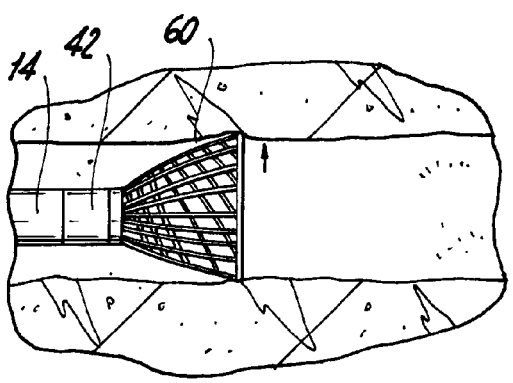

Referring to FIGS. 11a–11b, another embodiment of the fixation member is designated generally by reference numeral 60. Fixation member 60 is defined by a radially expandable vascular stent formed from a bio-compatible polymeric material or metal that may be braided or cut from a tubular structure. It is envisioned that the stent would move from a contracted position to a radially expanded position when exposed to body temperature, or in response to retracting a sheath (not shown) initially disposed about the stent during its placement within a blood vessel.

Figure 12:
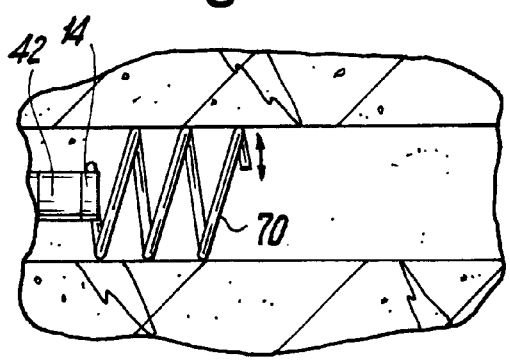
FIGS. 12 and 13 illustrate additional embodiments of an expandable fixation device operatively associated with the distal end portion of the inner lead body.
Figure 13:
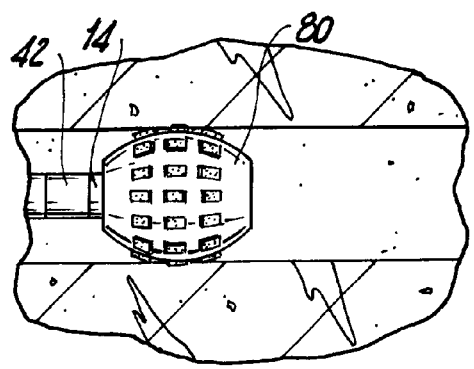

FIGS. 12 and 13 illustrate two other embodiments of a fixation member including a radially expandable cylindrical coil 70 and a radially expandable wire cage 80. These fixation devices may be constructed and deployed in a manner similar to fixation member 60. It is envisioned that the distal end portion 16 of the outer lead body 12 may also include a fixation member in the form of any one of the previously described fixation structures or at least one flexible tine as is known in the art. The fixation member associated with the distal end portion of the outer lead body 12 could be electrically active and/or provided with a coating containing a medicament.

Figure 8:
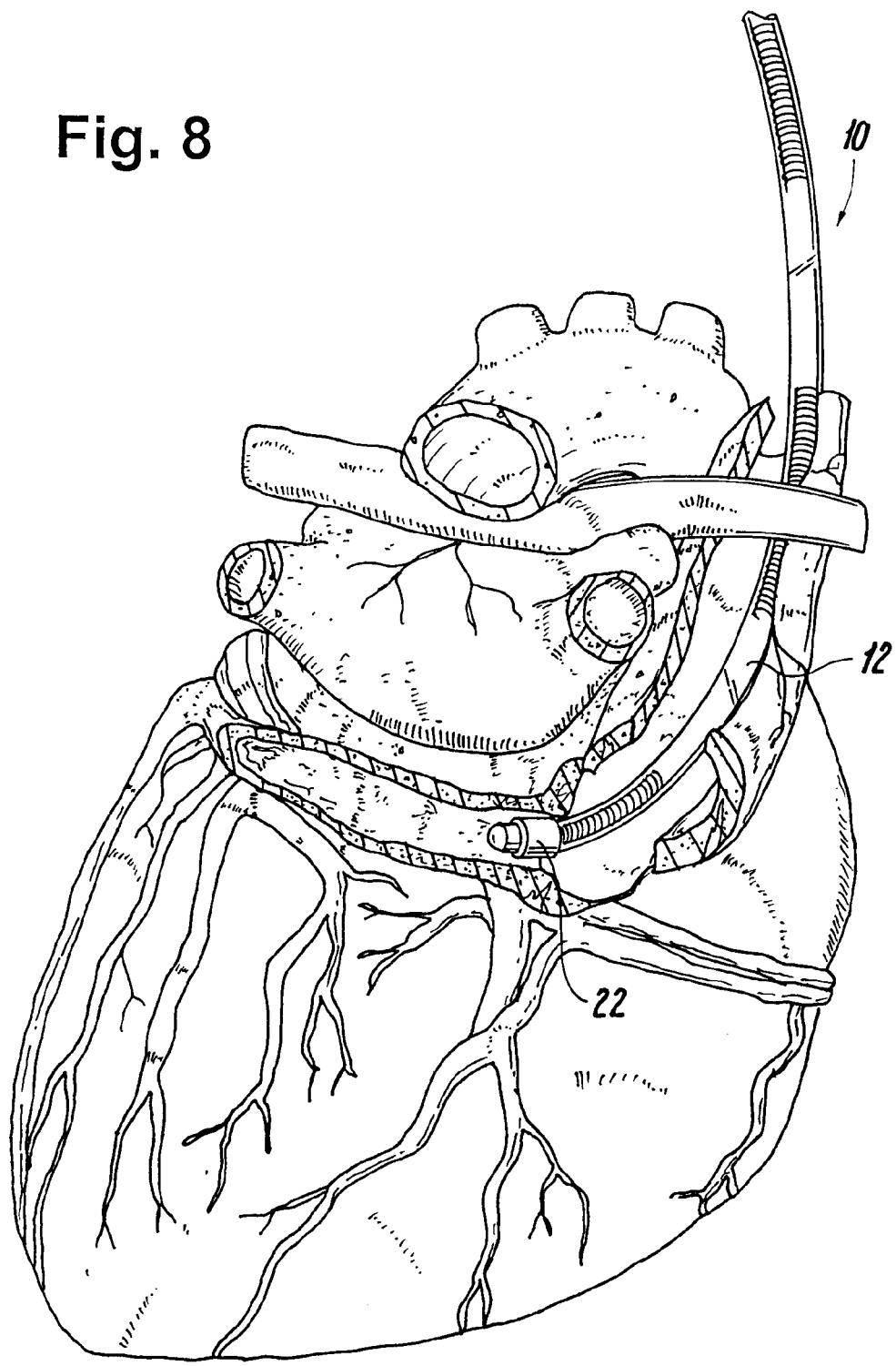
FIG. 8 illustrates the placement of the outer lead body of the coronary sinus lead of FIG. 5, through the superior vena cava to a position adjacent the auriculo-ventricular opening to the coronary sinus.
Figure 9:
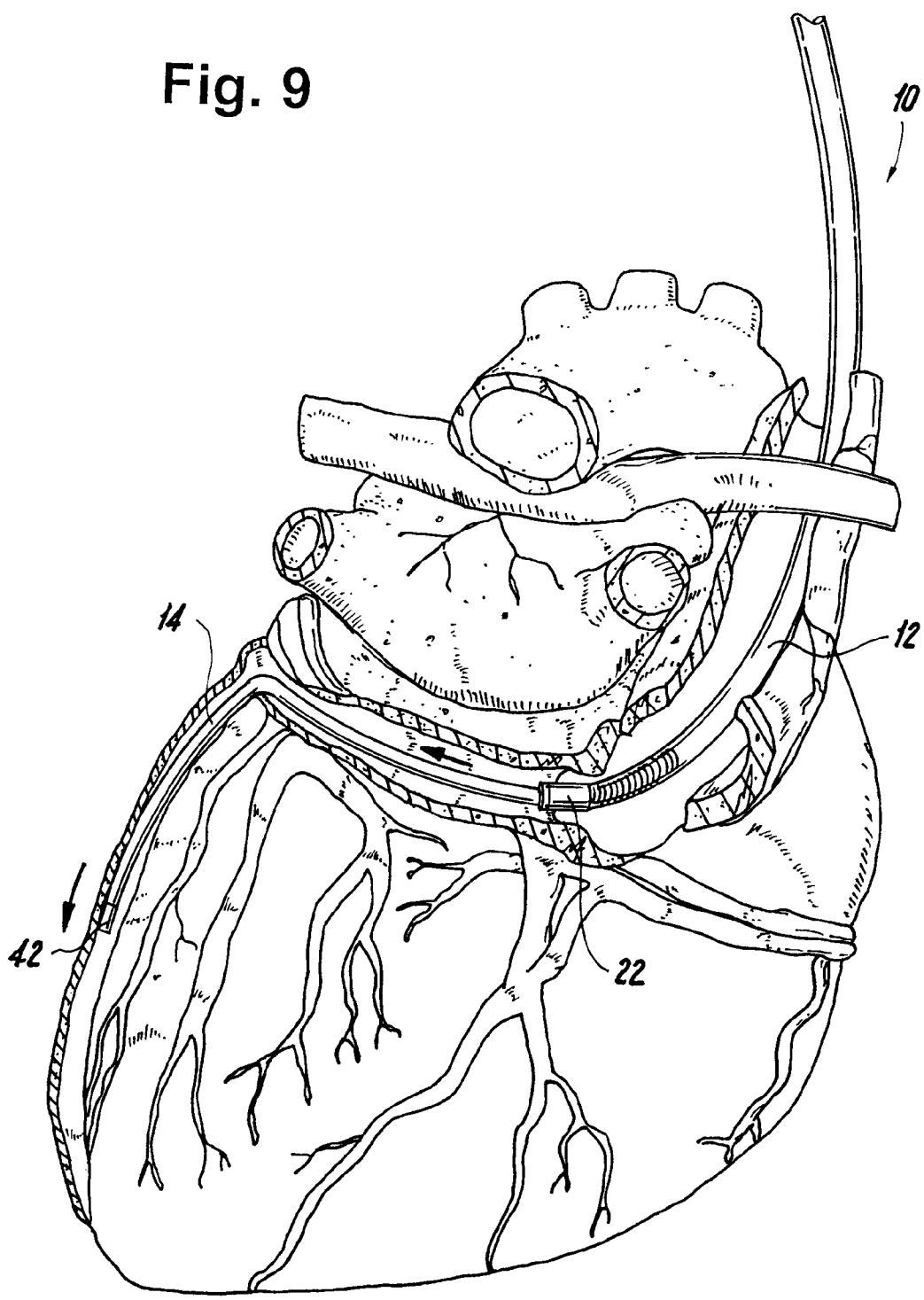
FIG. 9 illustrates the placement of the inner lead body through the interior lumen of the outer lead body and into the great cardiac vein of the heart through the coronary sinus.

Referring now to FIGS. 1, 5, 8 and 9, by way of example, coronary sinus lead 10 is deployed in the following manner for facilitating left ventricular pacing and/or sensing. Initially, as illustrated in FIG. 8, with the assistance of a guiding stylet or catheter (not shown), the outer lead body 12 is extended into the right atrium of the heart through the superior vena cava to a position adjacent to the auriculoventricular opening to the coronary sinus. At such time, the distal tip of the outer lead body 12 is in a closed or sealed condition. In this position, the distal ground electrode 22 (anode) of the outer lead body 12 is disposed within the right atrium. Thereafter, as illustrated in FIG. 9, the inner lead body 14 is introduced into the coronary sinus by way of the interior lumen 20 of the outer lead body 12. In essence, the outer lead body 12 serves as a guide catheter to facilitate the placement of the inner lead body 14 into the coronary sinus and subsequent introduction into the great cardiac vein or branch vein.

The inner lead body 14 is advanced into the great cardiac vein or branch vein to a location where the distal tip electrode 42 (cathode) is positioned so as to be in contact with the wall of the left ventricle, as best seen in FIG. 1. Then, as shown for example in FIG. 4, the proximal end portions 18, 38 of the outer and inner lead bodies 12, 14 are threadably connected to one another so as to form an integral structure. At such a time, either one of the fixation devices 50, 60, 70 or 80 may be deployed from the distal end portion 36 of the inner lead body 14 to prevent longitudinal displacement of lead 10. Furthermore, a similar fixation structure operatively associated with the distal end portion 16 of the outer lead body 12 may be deployed within the right atrium to maintain the position of lead 10. Once lead 10 has been fully deployed and the two lead bodies 12, 14 have been threadably connected to one another, the lead 10 is operatively connected to a cardiac pacemaker so that it may be employed for left ventricular pacing and/or sensing.

Figure 14:
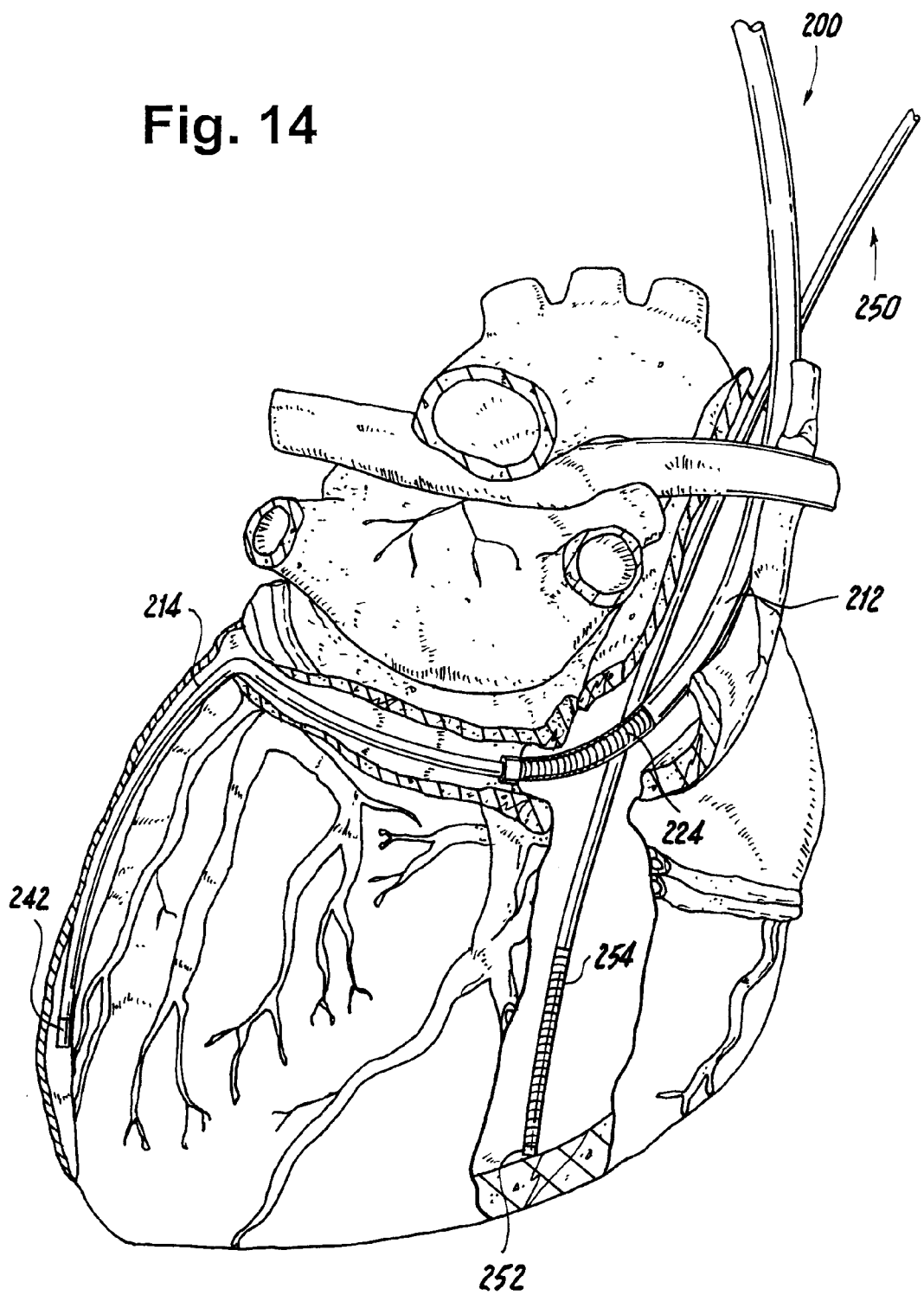
FIG. 14 illustrates the deployment of the coronary sinus lead of FIG. 6 which is configured for left ventricular pacing and sensing, in conjunction with a second lead configured for right ventricular pacing and sensing, as well as defibrillation.

Referring now to FIG. 14 in conjunction with FIG. 6, coronary sinus lead 200 is employed to facilitate left ventricular pacing and/or sensing in conjunction with a second lead 250 configured for right ventricular pacing and sensing, as well as defibrillation. More particularly, lead 200 is deployed in the manner described above with respect to lead 10. Lead 250 is extended into the right ventricle by way of the superior vena cava and is secured therein by a conventional fixation structure, such as, for example, a helical fixation screw. As illustrated, lead 250 includes a distal tip electrode 252 for pacing and/or sensing and a distal shock electrode 254 for right ventricular defibrillation. The ground for defibrillation is supplied by the elongated proximal electrode 224 of the outer lead body 212.

Figure 15:
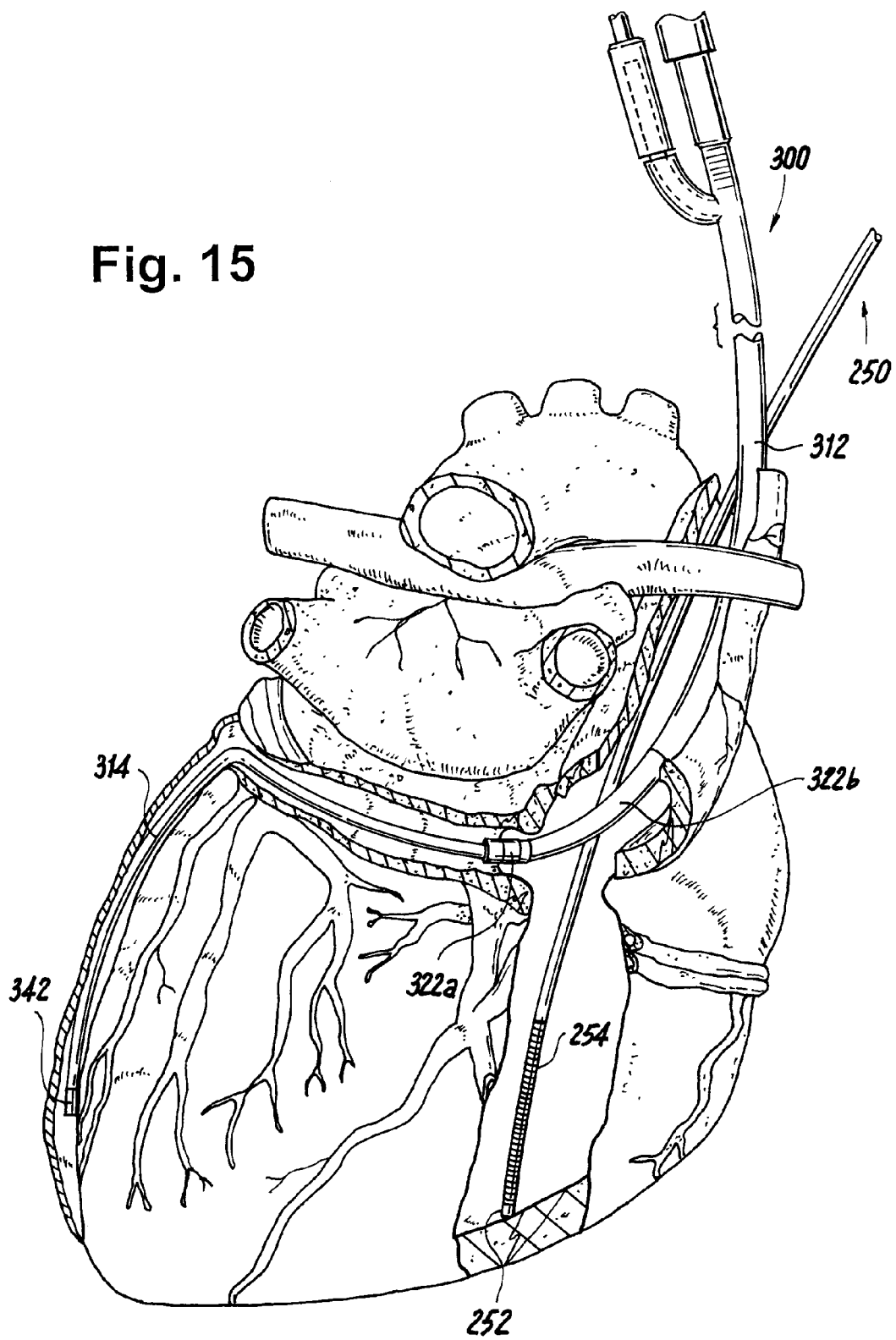
FIG. 15 illustrates the deployment of the coronary sinus lead of FIG. 7 which is configured for left ventricular and right atrial pacing and sensing, in conjunction with a second lead configured for right ventricular pacing and sensing, as well as defibrillation.

Referring to FIG. 15 in conjunction with FIG. 7, coronary sinus lead 300 is employed to facilitate left ventricular and right atrial pacing and sensing, in conjunction with a second lead configured for right ventricular pacing and sensing, as well as defibrillation. More particularly, lead 300, which is deployed in the manner described above with respect to lead 10 to facilitate left ventricular pacing and/or sensing, right atrial pacing and/or sensing, and right ventricular defibrillation. As in the previous deployment shown in FIG. 14, lead 250 is extended into the right ventricle by way of the superior vena cava and includes a distal tip electrode 252 for pacing and/or sensing and a distal shock electrode 254 for right ventricular defibrillation in conjunction with the proximal ground electrode 322b of outer lead body 312.

Figure 16:
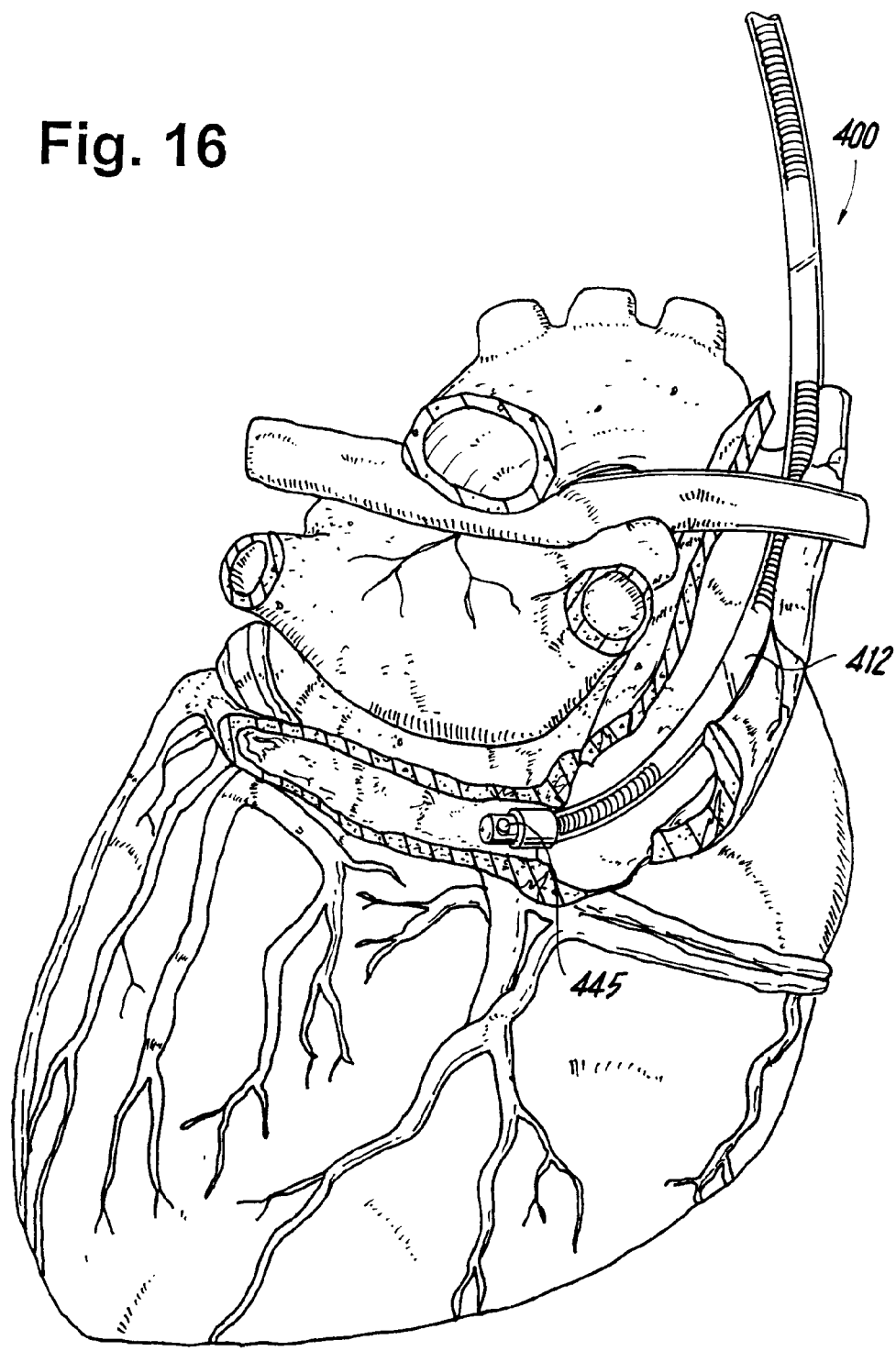
FIG. 16 illustrates another embodiment of the coronary sinus lead of the subject invention wherein the a sensor is operatively associated with the distal end portion of the outer lead body for measuring blood flow parameters to facilitate placement of the distal end portion of the outer lead body adjacent the opening to the coronary sinus.

Referring now to FIG. 16, there is illustrated another embodiment of the coronary sinus lead of the subject invention designated generally by reference numeral 400. In this embodiment, the distal end portion of the outer lead body includes a sensor 445 for monitoring blood flow parameters. The blood flow sensor 445 can take the form of an ultrasonic pulse Doppler sensor, transit-time sensor or a similar sensor. Such sensors are known in the art as disclosed for example in U.S. Pat. No. 5,409,009 to Olson, the disclosure of which is herein incorporated by reference in its entirety.

Although the coronary sinus lead and placement method of the subject invention has been described with respect to preferred embodiments, those skilled in the art will readily appreciate that changes and modifications may be made thereto without departing from the spirit and scope of the present invention as defined by the appended claims.

What is claimed is:

1. A cardiac lead comprising:
   a) a first elongated lead body having opposed proximal and distal end portions and having an interior lumen extending therethrough, the first lead body including means operatively associated with the distal end portion thereof for measuring blood flow parameters to facilitate placement of the distal end portion of the first lead body adjacent the coronary sinus, and having at least one distal electrode operatively associated with the distal end portion thereof and a proximal electrode operatively associated with the proximal end portion thereof; and
   b) a second elongated lead body having opposed proximal and distal end portions, the second lead body having at least one distal electrode operatively associated with the distal end portion thereof and a proximal electrode operatively associated with the proximal end portion thereof, wherein the second elongated lead body is dimensioned and configured for accommodation within the interior lumen of the first lead body.

2. A cardiac lead as recited in claim 1, wherein the means operatively associated with the distal end portion of the first lead body for measuring blood flow parameters is defined by a blood flow sensor.

3. A cardiac lead as recited in claim 1, wherein the second lead body has a length that is greater than the length of the first lead body.

4. A cardiac lead as recited in claim 1, wherein a conductor extends through the first lead body to connect the distal electrode and the proximal electrode.

5. A cardiac lead as recited in claim 1, wherein a conductor extends through the second lead body to connect the distal electrode and the proximal electrode.

6. A cardiac lead as recited in claim 1, wherein the second lead body has an interior lumen extending therethrough.

7. A cardiac lead as recited in claim 1, wherein the distal electrode of the first lead body is a ring electrode.

8. A cardiac lead as recited in claim 1, wherein the distal electrode of the first lead body is a coil electrode.

9. A cardiac lead as recited in claim 1, wherein the distal electrode of the first lead body is a ground electrode.

10. A cardiac lead as recited in claim 1, wherein the distal electrode of the second lead body is a ring electrode.

11. A cardiac lead as recited in claim 1, wherein the distal electrode of the second lead body is a tip electrode.

12. A cardiac lead as recited in claim 1, wherein the distal electrode of the first lead body is anodic, and the distal electrode of the second lead body is cathodic.

13. A cardiac lead as recited in claim 1, wherein the proximal electrode of the second lead body is a pin connector.

14. A cardiac lead as recited in claim 1, wherein the first lead body includes seal means for sealing the interior lumen of the first lead body during insertion of the first lead body through the coronary venous system.

15. A cardiac lead as recited in claim 1, wherein the proximal end portion of the first lead body and the proximal end portion of the second lead body include means for connecting the first lead body to the second lead body.

16. A cardiac lead as recited in claim 15, wherein the means for connecting the first lead body to the second lead body includes a threaded connector.

17. A cardiac lead comprising:
  a) a first elongated lead body having opposed proximal and distal end portions and having an interior lumen extending therethrough, the first lead body having a sensor operatively associated with the distal end portion thereof for measuring blood flow parameters to facilitate placement of the distal end portion of the first lead body adjacent the coronary sinus, and having at least one distal electrode operatively associated with the distal end portion thereof and a proximal electrode operatively associated with the proximal end portion thereof; and
  b) a second elongated lead body having opposed proximal and distal end portions, the second lead body having at least one distal electrode operatively associated with the distal end portion thereof and a proximal electrode operatively associated with the proximal end portion thereof, wherein the second elongated lead body is dimensioned and configured for accommodation within the interior lumen of the first lead body.

* * * * *